(12) United States Patent
Liu

(10) Patent No.: US 9,399,794 B2
(45) Date of Patent: Jul. 26, 2016

(54) METHOD OF DETECTING NUCLEIC ACID TARGETS USING A STATISTICAL CLASSIFIER

(71) Applicant: Roche Molecular Systems, Inc., Pleasanton, CA (US)

(72) Inventor: Wei-Min Liu, Dublin, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 632 days.

(21) Appl. No.: 13/865,316

(22) Filed: Apr. 18, 2013

(65) Prior Publication Data

US 2013/0280712 A1 Oct. 24, 2013

Related U.S. Application Data

(60) Provisional application No. 61/635,192, filed on Apr. 18, 2012.

(51) Int. Cl.
| | |
|---|---|
| *G01N 33/48* | (2006.01) |
| *C12Q 1/68* | (2006.01) |
| *G06F 19/24* | (2011.01) |

(52) U.S. Cl.
CPC ............ *C12Q 1/6827* (2013.01); *C12Q 1/6848* (2013.01); *G06F 19/24* (2013.01)

(58) Field of Classification Search
CPC ....................................................... G06F 19/24
USPC ............................................................ 702/19
See application file for complete search history.

(56) References Cited

U.S. PATENT DOCUMENTS 7,598,052 B2 * 10/2009 Giordano ............. C12Q 1/6886
435/6.16

FOREIGN PATENT DOCUMENTS

| EP | 13164176 | 6/2013 |
| WO | 2010070637 A2 | 6/2010 |
| WO | 2010073248 A2 | 7/2010 |

* cited by examiner

*Primary Examiner* — Jerry Lin

(74) *Attorney, Agent, or Firm* — Kilpatrick Townsend & Stockton LLP

(57) ABSTRACT

A method of detecting a target nucleic acid in a test sample utilizes a learning statistical classifier system to build a general linear classifier based on an amplification-dependent parameter for the target and the control nucleic acids, in order to classify the test sample as containing or not containing the target nucleic acid.

20 Claims, 15 Drawing Sheets

METHOD OF DETECTING NUCLEIC ACID TARGETS USING A STATISTICAL CLASSIFIER

BACKGROUND OF THE INVENTION

Real-time polymerase chain reaction (PCR) has become an important tool in a variety of fields, ranging from medical diagnostics, to forensics and food safety monitoring. The advantages of current PCR technology are rapid detection, qualitative as well as quantitative information and high sensitivity and specificity. These features have made the real-time PCR a technology of choice in fields ranging from pathogen detection to testing for oncogenic mutations in the emerging field of personalized healthcare. See L. Peterson, (2011) *Molecular laboratory tests for the diagnosis of respiratory tract infection due to Staphylococcus aureus.* Clin. Infect. Dis.; 52 Suppl. 4:S361, S. Anderson, (2011) *Laboratory methods for KRAS mutation analysis.* Expert Rev. Mol. Diag.; 11:635. Many real-time PCR tests have been validated and harmonized to become standard tools used by hospitals and large-throughput commercial laboratories. However, PCR does have its limitations. With the daily running of PCR assays by a diagnostic laboratory, the problems of false-negative and false-positive results quickly become apparent. See J. Maurer, (2011) *Rapid detection and limitations of molecular techniques.* Ann. Rev. Food Sci. Technol.; 2:259. Many errors result from poor quality of the collected sample. However, the use of a better mathematical or statistical model during data analysis holds the promise of overcoming at least some of the problems associated with poor input material. See M. Sivaganesan et al., (2010) *Improved strategies and optimization of calibration models for real-time PCR absolute quantification.* Water Res.; 44:4726.

As an output of a real-time PCR-based diagnostic method, a sample is sometimes classified into one of several categories: mutant and wild-type, infected and not infected, etc. Sensitivity of a method is reduced when samples fall into the "grey area" where the signal appears present but too close to the minimum threshold to be classified into any of the groups. The unclassified pool represents potentially false-negative and false-positive samples for whom the real-time PCR test has failed to deliver an answer. The present invention provides a better statistical tool for minimizing the number of unclassified samples in real-time PCR tests.

SUMMARY OF THE INVENTION

In one embodiment, the present invention is a method of detecting the presence or absence of a target nucleic acid in a test sample comprising: inputting into a learning statistical classifier system data from a training set of samples where the amount of the target nucleic acid and a control nucleic acid is known, using the learning statistical classifier system, calculating a plurality of weights for a general linear classifier; building a general linear classifier with the plurality of weights calculated by the learning statistical classifier system; contacting the test sample with a reaction mixture containing reagents necessary to amplify the target and the control nucleic acids by polymerase chain reaction (PCR) under conditions enabling PCR; measuring at least one amplification-dependent parameter for the target and the control nucleic acids to obtain a test set of data; applying the general linear classifier to the test set of data to classify the test sample as containing or not containing the target nucleic acid, thereby detecting the presence or absence of the target nucleic acid in the test sample. In variations of this embodiment, the learning statistical classifier system is selected from SVM, LDA and QDA. In further variations of this embodiment, the amplification-dependent parameter is fluorescence detected during each cycle of amplification. In further variations of this embodiment, the data is cycle-to-threshold ($C_t$) value. In further variations of this embodiment, the general linear classifier is a piece-wise linear classier. In further variations of this embodiment, a piece-wise function determined by constraints placed upon the amplification-dependent parameter for the control nucleic acid is input into the piece-wise linear classifier. In further variations of this embodiment, the target nucleic acid is a nucleic acid variant of a human sequence.

In another embodiment, the invention is a method of detecting the presence or absence of a target nucleic acid in a test sample comprising: inputting into a learning statistical classifier system data from a training set of samples where the amount of the target nucleic acid and a control nucleic acid is known; using the learning statistical classifier system, calculating a plurality of weights for a general linear classifier; building a general linear classifier with the plurality of weights calculated by the learning statistical classifier system; subjecting the sample to polymerase chain reaction (PCR); measuring at least one amplification-dependent parameter for the target and the control nucleic acids to obtain a test set of data; applying the general linear classifier to the test set of data; classifying the test sample as containing or not containing the target nucleic acid, thereby detecting the presence or absence of the target nucleic acid in the test sample. In variations of this embodiment, the learning statistical classifier system is selected from SVM, LDA and QDA. In further variations of this embodiment, the amplification-dependent parameter is fluorescence detected during each cycles of amplification. In further variations of this embodiment, the data is cycle-to-threshold ($C_t$) value. In further variations of this embodiment, the general linear classifier is a piece-wise linear classifier. In further variations of this embodiment, a piece-wise function determined by constraints placed upon the amplification-dependent parameter for the control nucleic acid is input into the piece-wise linear classifier. In further variations of this embodiment the target nucleic acid is a nucleic acid variant of a human sequence.

In another embodiment, the invention is a method of determining whether a target nucleic acid is present in a test sample comprising: subjecting a training set of samples wherein the amount of the target nucleic acid and a control nucleic acid is known to polymerase chain reaction (PCR) and measuring at least one amplification-dependent parameter for the target and the control nucleic acids to obtain a training set of data; inputting the data into a learning statistical classifier system; using the learning statistical classifier system, calculating a plurality of weights for a general linear classifier; building a general linear classifier with the plurality of weights determined by the learning statistical classifier system; subjecting the test sample to PCR and measuring at least one amplification-dependent parameter for the target and the control nucleic acids to obtain a test set of data; applying the general linear classifier to the test set of data; classifying the test sample as containing or not containing the target nucleic acid. In variations of this embodiment, the learning statistical classifier system is selected from SVM, LDA and QDA. In further variations of this embodiment, the amplification-dependent parameter is fluorescence detected during each cycles of amplification. In further variations of this embodiment, the data is cycle-to-threshold ($C_t$) value. In further variations of this embodiment, the general linear classifier is a piece-wise linear classifier. In further variations of this embodiment, a piece-wise function determined by constraints placed upon the amplification-dependent parameter for the control nucleic acid is input into the piece-wise linear classifier. In further variations of this embodiment the target nucleic acid is a nucleic acid variant of a human sequence.

In another embodiment, the invention is a method of determining whether a target nucleic acid is present in a test sample comprising: subjecting a training set of samples wherein the amount of the target nucleic acid and a control nucleic acid is known to polymerase chain reaction (PCR) and measuring at least one amplification-dependent parameter for the target and the control nucleic acids to obtain a training set of data; inputting the data into a learning statistical classifier system; using the learning statistical classifier system, calculating a plurality of weights for a general linear classifier; building a general linear classifier with the plurality of weights determined by the learning statistical classifier system; subjecting the test sample to PCR and measuring at least one amplification-dependent parameter for the target and the control nucleic acids to obtain the test set of data; applying the general linear classifier to the test set of data obtained; classifying the test sample as containing or not containing the target nucleic acid. In variations of this embodiment, the learning statistical classifier system is selected from SVM, LDA and QDA. In further variations of this embodiment, the amplification-dependent parameter is fluorescence detected during each cycles of amplification. In further variations of this embodiment, the data is cycle-to-threshold ($C_t$) value. In further variations of this embodiment, the general linear classifier is a piece-wise linear classifier. In further variations of this embodiment, a piece-wise function determined by constraints placed upon the amplification-dependent parameter for the control nucleic acid is input into the piece-wise linear classifier. In further variations of this embodiment the target nucleic acid is a nucleic acid variant of a human sequence.

In yet another embodiment, the invention is a computer readable medium including code for controlling one or more processors to classify whether a test sample contains a target nucleic acid, the code including instructions to: apply a learning statistical classifier system to a training data set where the amount of the target nucleic acid and a control nucleic acid is known, in order to build a general linear classifier of Formula I; apply the general linear classifier to a testing data set comprising the data from the test sample to produce a statistically derived decision classifying the test sample as containing or not containing the target nucleic acid. In variations of this embodiment, the learning statistical classifier system is selected from SVM, LDA and QDA. In further variations of this embodiment, the data in the datasets is cycle-to-threshold ($C_t$) value. In further variations of this embodiment, the general linear classifier is a piece-wise linear classifier. In further variations of this embodiment the target nucleic acid is a nucleic acid variant of a human sequence.

In yet another embodiment, the invention is a system for detecting a target nucleic acid in a test sample comprising: a data acquisition module configured to produce a data set from a training set of samples and one or more test samples, the data set indicating presence and amount of the target nucleic acid and a control nucleic acid; a data processing unit configured to process the data acquired by the acquisition module by applying a learning statistical classifier system to the training data set in order to build a general linear classifier of Formula I, and then apply the general linear classifier of Formula I to the test data set comprising the data from the test sample, to produce a statistically derived decision classifying the test sample as containing or not containing the target nucleic acid; a display module configured to display the data produced by the data processing unit. In variations of this embodiment, the learning statistical classifier system is selected from SVM, LDA and QDA. In further variations of this embodiment, the general linear classifier is a piece-wise linear classifier.

DETAILED DESCRIPTION OF THE INVENTION

Definitions

Figure 1A:
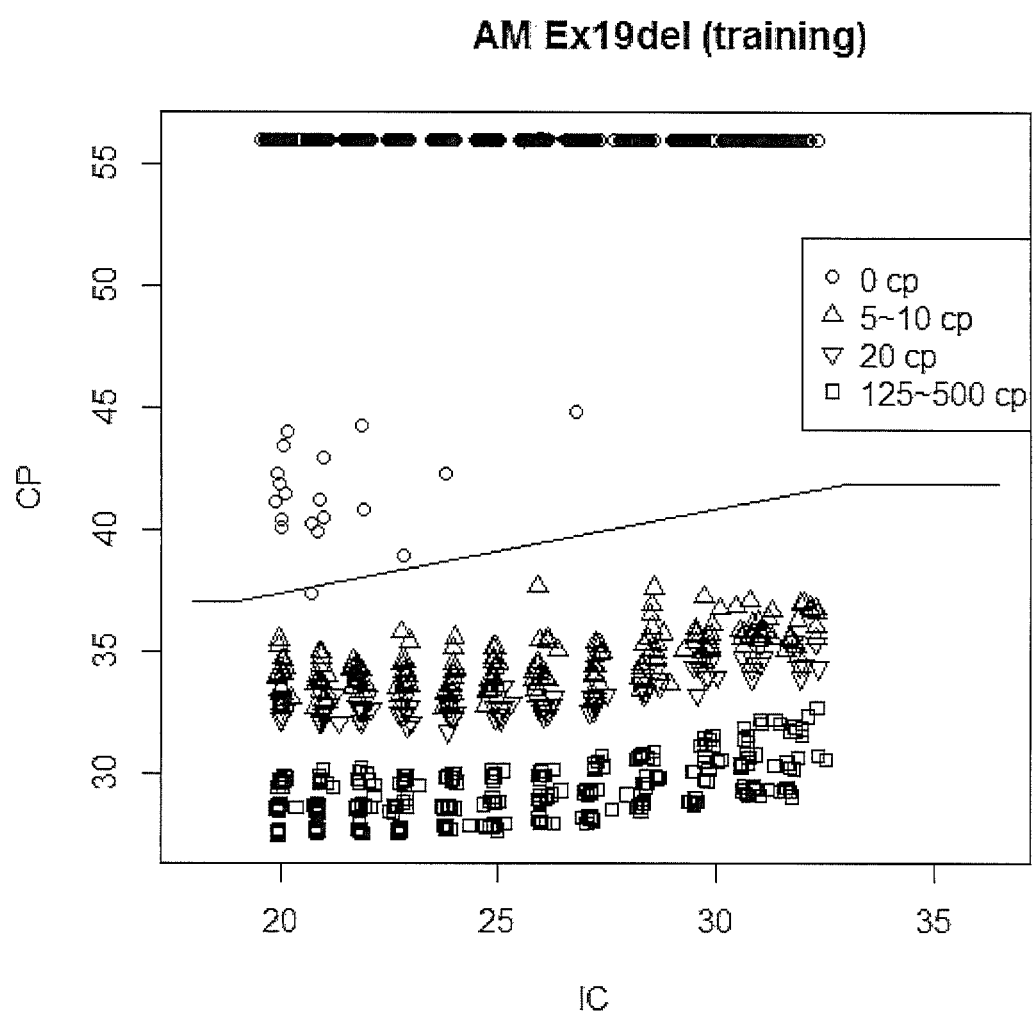
FIG. 1A. Relationship between the $C_t$ values for the target and control nucleic acids for the EGFR Exon 19 deletion target (training data set).

The term "constraint" means an experimentally determined constant that defines a desired range of a variable associated with samples such that within the range, the true positive and true negative samples can be satisfactorily distinguished. For example, constraint could be an experimentally determined constant that defines a desired range of $C_t$ values for the internal control (IC values) where the true positive and true negative samples in the training set have reduced overlaps of their $C_t$ values (CP values). The range defined by one or more constraints may be open or closed.

The term "growth curve" in the context of a nucleic acid amplification assay is a graph of a function, where an independent variable is the number of amplification cycles and a dependent variable is an amplification-dependent measurable parameter measured at each cycle of amplification. Typically, the amplification-dependent measurable parameter is the amount of fluorescence emitted by the probe upon hybridization, or upon the hydrolysis of the probe by the nuclease activity of the nucleic acid polymerase, see Holland et al., (1991) Proc. Natl. Acad. Sci. 88:7276-7280 and U.S. Pat. No. 5,210,015. In a typical polymerase chain reaction, a growth curve comprises a segment of exponential growth followed by a plateau. A growth curve is typically characterized by a "cycles to threshold" value or "$C_t$" value, which is a number of cycles where a predetermined magnitude of the measurable parameter is achieved. A lower $C_t$ value represents more rapid completion of amplification, while the higher $C_t$ value represents slower completion of amplification. Where the efficiency of amplification is similar, the lower $C_t$ value is reflective of the higher starting amount of the target nucleic acid, while the higher $C_t$ value is reflective of the lower starting amount of the target nucleic acid. Where a control nucleic acid of known concentration is used, it becomes possible to determine the absolute amount of the target nucleic acid by comparing the $C_t$ values of the target and control nucleic acids.

The terms "internal control nucleic acid" or simply "control nucleic acid" refer to a nucleic acid sequence distinct from the target nucleic acid sequence that is also present in the sample. The internal control sequence may or may not be present on the same nucleic acid molecule as the target sequence. Typically, the internal control requires separate primers and probes distinct from primers and probes that hybridize to the target nucleic acid.

The terms "nucleic acid," "polynucleotide" and "oligonucleotide" refer to target sequences, primers and probes. The terms are not limited by length and are generic to linear polymers of deoxyribonucleotides (single-stranded or double-stranded DNA), ribonucleotides (RNA), and any other N-glycoside of a purine or pyrimidine base, including adenosine, guanosine, cytidine, thymidine and uridine and modifications of these bases.

The term "primer" refers to an oligonucleotide that acts as a point of initiation of DNA synthesis under suitable conditions in the presence of nucleic acid precursors and an agent for polymerization. A primer can either consist entirely of the target-hybridizing region or can contain additional features which allow for detection, immobilisation, or manipulation of the amplified product.

The term "probe" refers to a nucleic acid that selectively hybridizes to a target nucleic acid under suitable conditions. A probe can either consist entirely of the target-hybridizing region or can contain additional features which allow for the detection, immobilization, or manipulation of the probe-target duplex. The probe may contain modifications to its primary structure by the addition of labels, linkers, peptides or any other groups necessary to perform the detection assay in the chosen format.

The terms "target sequence" or "target" refer to a region of a nucleic acid that is to be analyzed.

The term "sample" refers to any composition containing or presumed to contain nucleic acid. This includes a sample of tissue or fluid isolated from an individual for example, skin, plasma, serum, spinal fluid, lymph fluid, synovial fluid, urine, tears, blood cells, organs and tumors, including the fresh-frozen tissue and formalin-fixed paraffin embedded tissue (FFPET), and also to samples of in vitro cultures established from cells taken from an individual, and nucleic acids isolated therefrom.

The terms "training set" or "training data set" refer to a set of samples used to establish a correlation between two variables and build a statistical model. For example, a training set is a set of samples where the presence or absence of various amounts of target nucleic acid is known that is used to establish a correlation between the $C_t$ value in real-time PCR and presence or absence of the target nucleic acid in the sample.

The terms "testing set" or "testing data set" refer to a set of one or more samples used to verify the correlation established using the training set. For example, a testing set is a set of samples where the presence or absence of various amounts of target nucleic acid is known. This set is used to verify whether the correlation between the $C_t$ value in real-time PCR and presence or absence of the target nucleic acid established using the training set will correctly predict presence or absence of the target nucleic acid.

The term "test sample" refers to a sample for example, a patient's sample that is to be tested for a particular parameter.

The present invention comprises a statistical tool for detecting a target nucleic acid in the sample that minimizes the number of unclassified samples in real-time PCR tests. A diagnostic method employing real-time PCR typically comprises amplification of the nucleic acids and detection of an amplification-dependent signal, followed by automated data analysis and generation of an output for the user. Some tests deliver quantitative data reporting the amount of the target nucleic acid in the sample for example, the amount of viral nucleic acid ("viral load,") or proportion of mutated cells. In other tests, quantitative data gathered from the amplification reaction is converted into a qualitative result where the sample is classified into one of several categories: mutant and wild-type, infected and not infected, etc. In a typical real-time PCR, the amplification-dependent signal is fluorescence emitted by a labeled probe upon hybridization, or upon hydrolysis of the probe by the nuclease activity of the nucleic acid polymerase, see Holland et al., (1991) Proc. Natl. Acad. Sci. 88:7276-7280 and U.S. Pat. No. 5,210,015. The data analysis involves using the fluorescence data to generate a growth curve and calculate a $C_t$ value for each target sequence. The final output of the data analysis may be quantitative and report the amount of the target nucleic acid in the sample calculated based on the $C_t$ value. The output may also be qualitative and report simply whether or not the target nucleic acid is present in the sample. The qualitative result is also based on the $C_t$ value: the target nucleic acid is deemed present if the $C_t$ value falls below a predetermined threshold.

The relationship between $C_t$ value and the amount of the target in the sample is not a simple one. When reaction efficiencies differ among samples, for example due to the presence of inhibitors or poor quality of the input nucleic acid, the $C_t$ value may not accurately reflect the starting amount (or even presence) of the target nucleic acid. An internal control is often used to assess efficiency of the reaction. A typical real-time PCR data analysis algorithm uses statistical tools to establish a more accurate relationship between the $C_t$ value and the presence or amount of the target nucleic acid in the sample and generate a user-readable qualitative or quantitative report.

The present invention comprises a data analysis algorithm for real-time PCR that uses a learning statistical classifier system to build a general linear classifier that delivers a qualitative output reporting the presence or absence of a target nucleic acid in a sample. The general linear classifier (Formula 1) comprises a plurality of weights (w[1, 2, 3 . . . ])

calculated using a training set of samples and the learning statistical classifier system. An example of a learning statistical classifier system is support vector machine (SVM) algorithm (Cortes, C. and Vapnik, V. (1995) Machine Learning, 20:273-297). Other examples include linear discriminant analysis (LDA) and quadratic discriminant analysis (QDA) (Duda, R., Hart, P., and Stork, D. (2000). *Pattern Classification* (2$^{nd}$ ed.), Wiley, NY.; Hastie, T., Tibshirani, R., and Friedman, J. (2001). *The Elements of Statistical Learning: Data Mining, Inference, and Prediction*, Springer-Verlag, NY., pp. 84-95. Many other examples of learning statistical classifier systems will be apparent to one skilled in statistical arts.

$$F(x)=w[0]+w[1]*x[1]+w[2]*x[2] \qquad \text{Formula 1}$$

where $F(x)$ is the decision function for sample x, $x[1]$ is $C_t$ value for the target nucleic acid, $x[2]$ is $C_t$ value for the control nucleic acid, and $w[0]$, $w[1]$ and $w[3]$ are constants determined using SVM.

By comparison, existing methods use a special linear classifier in the real-time PCR analysis algorithm. The special linear classifier is a species of the general linear classifier where $w[2]=-w[1]$ and $A=w[0]/w[1]$. The classifier may be described by Formula 2:

$$G(x)=x[1]-x[2]-A \qquad \text{Formula 2}$$

where $G(x)$ is the decision function, $x[1]$ is $C_t$ value for the target nucleic acid, $x[2]$ is $C_t$ value for the control nucleic acid and $A=w[0]/w[1]$.

In some embodiments, $C_t$ value for the target nucleic acid is converted into a relative value according to Formula 3:

$$RCP=CP-IC \qquad \text{Formula 3}$$

where RCP is relative $C_t$ value for the target nucleic acid, CP is $C_t$ value for the target nucleic acid, and IC is $C_t$ value for the control nucleic acid.

If Formula 3 is used, then accordingly, in Formula 1, $x[1]=RCP$ and $x[2]=IC$.

The classifier of Formula I utilizes the data from a control nucleic acid. The control nucleic acid is necessary to gauge the presence and quality of the input nucleic acids in the sample. Control nucleic acid is generally a sequence necessarily present in the target genome. Therefore detection of the control nucleic acid confirms that the nucleic acids from the target genome are present in the sample and are sufficiently pure and intact to allow amplification by PCR. The absence of a signal from the control nucleic acid signifies that poor quality of the sample precludes successful testing. In some embodiments of the present invention, control nucleic acid is a part of the same gene as the target nucleic acid. However, control nucleic acid may be located anywhere in the genome of the organism to be tested. Optionally, control nucleic acid is present at the same copy number in the target genome as the control nucleic acid. In some embodiments, control nucleic acid requires PCR primers and probes distinct from the primers and probes required for the amplification and detection of the target nucleic acid. However, where sequence context permits, it is also possible that the control and the target nucleic acids share one or more primers and probes.

To build a classifier according to Formula 1, a training set of samples where the presence of various amounts or absence of the target nucleic acid and a control nucleic acid is known is subjected to PCR that amplifies both the target and the control nucleic acids. According to the method of the present invention, $C_t$ values for the target nucleic acid and the control nucleic acid (or RCP, CP and IC according to Formula 3) are imported into a learning statistical classifier system, such as for example, SVM so that a plurality of weights can be generated.

The weights determined by the learning statistical classifier system are then used in a general linear classifier according to Formula 1. When the decision function determined according to Formula 1 is positive or negative ($F(x)>0$, or $F(x)<0$), the sample is classified into one of the two corresponding classes, e.g. containing the target nucleic acid or not containing the target nucleic acid. If the decision function is zero ($F(x)=0$), the sample has no call.

In one embodiment, the classifier can be further optimized to minimize error of the classifier. In variations of this embodiment, the classifier can be optimized by selecting one or more constraints. For example, constraints can be placed on the $C_t$ value of the internal control nucleic acid (IC). A single constraint setting a cut-off value or two constraints setting a range of values can be set. If a sample in the training set has a $C_t$ value for the control nucleic acid (IC) falling outside the constraints, the sample is not used in the model. In some embodiments, a single lower cut-off value (M) is used (i.e. samples with the IC<M are excluded). In other embodiments, a single upper cut-off value (N) is used (i.e. samples with the IC>N are excluded). In yet other embodiments, a range using the upper and the lower cut-off values is set (i.e. only samples with $M \leq IC \leq N$ are used and the rest are excluded).

Figure 1B:
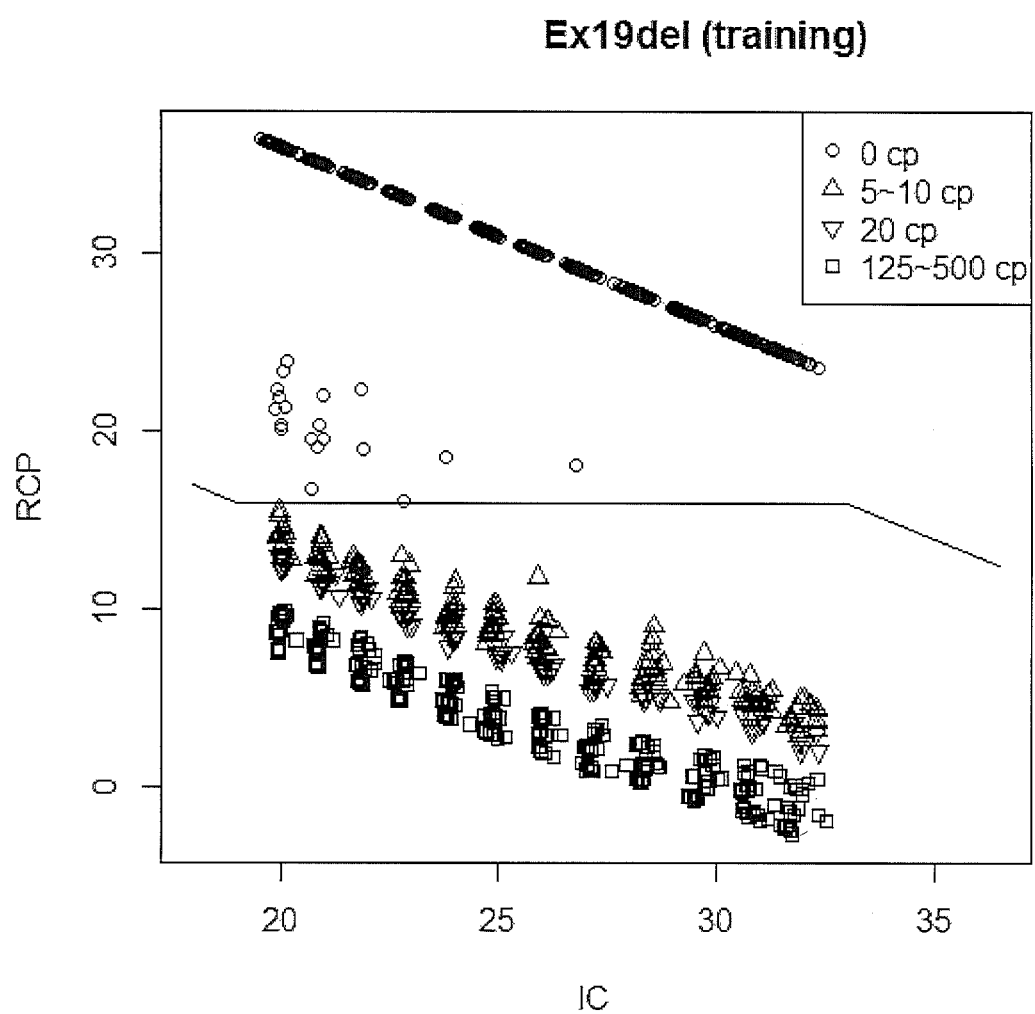
FIG. 1B. Relationship between the relative $C_t$ value for the target nucleic acid and the $C_t$ value for the control nucleic acid for the EGFR Exon 19 deletion target (training data set).
Figure 1C:
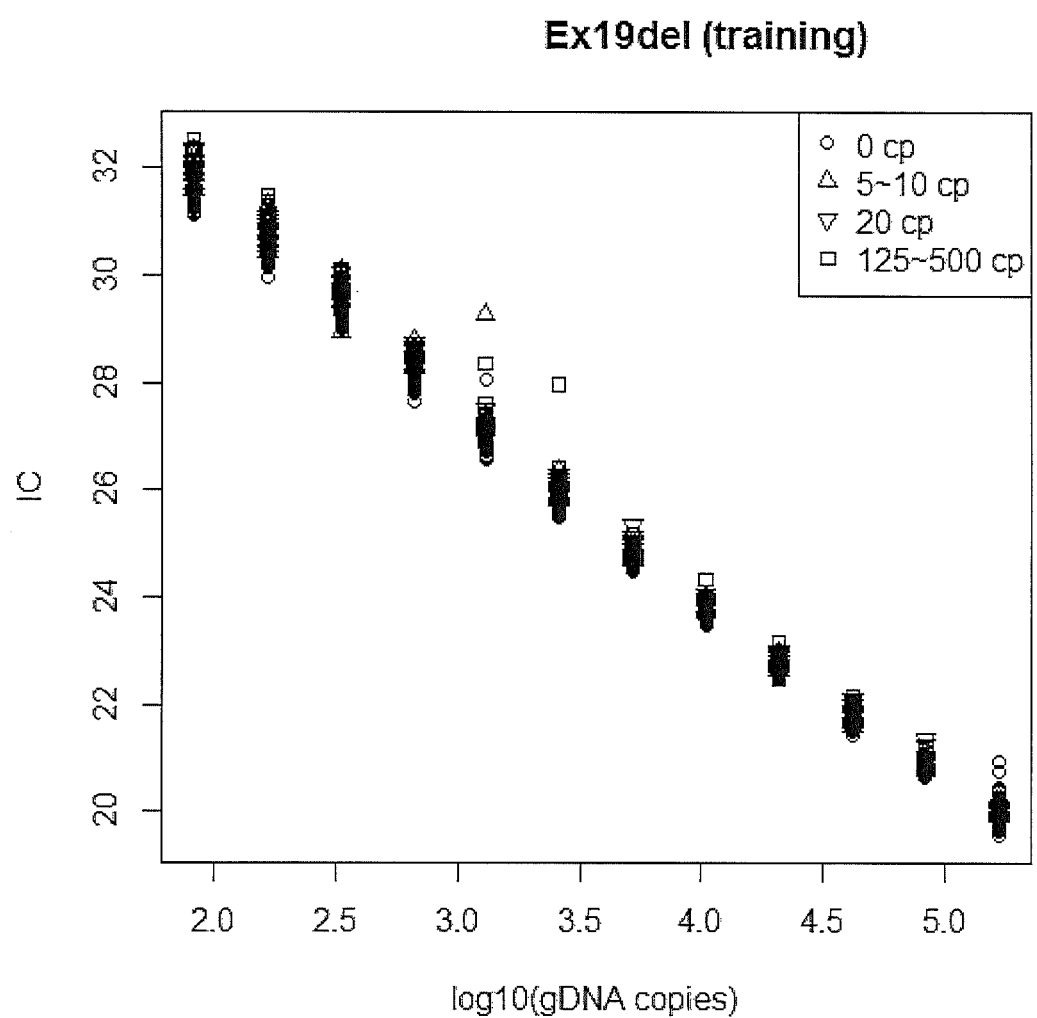
FIG. 1C. Relationship between the $C_t$ value for the control nucleic acid and initial DNA input for the EGFR Exon 19 deletion target (training data set).
Figure 2A:
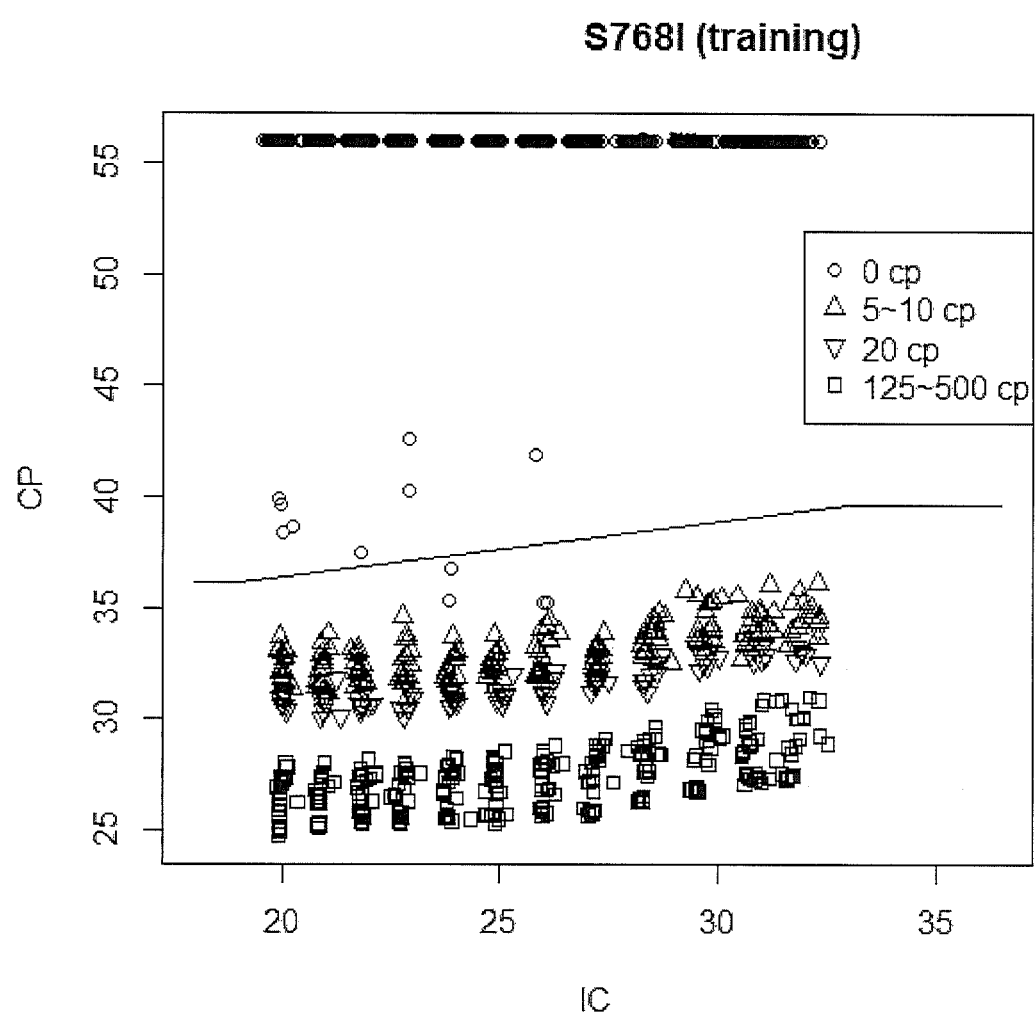
FIG. 2A. Relationship between the $C_t$ values for the target and control nucleic acids for the EGFR mutation S786I target (training data set).
Figure 2B:
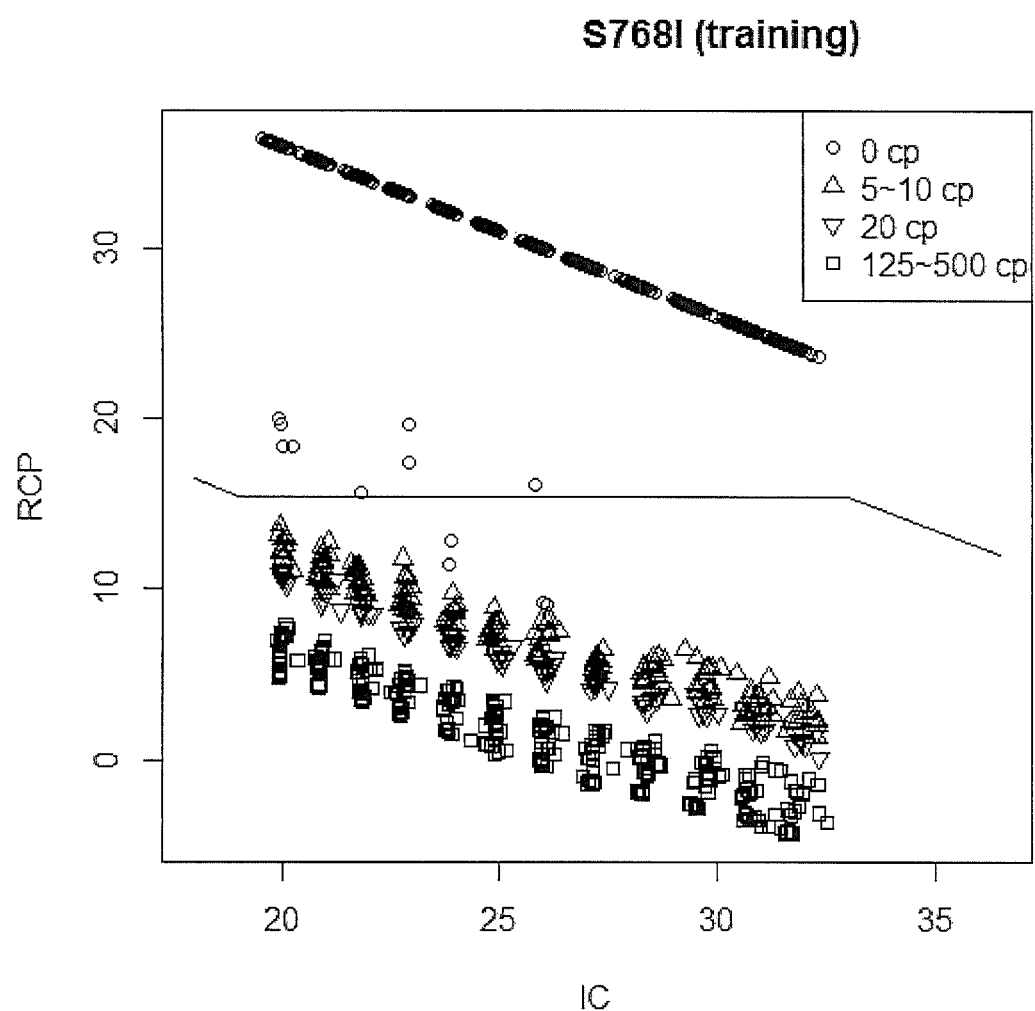
FIG. 2B. Relationship between the relative $C_t$ value for the target nucleic acid and the $C_t$ value for the control nucleic acid for the EGFR mutation S786I target (training data set).
Figure 2C:
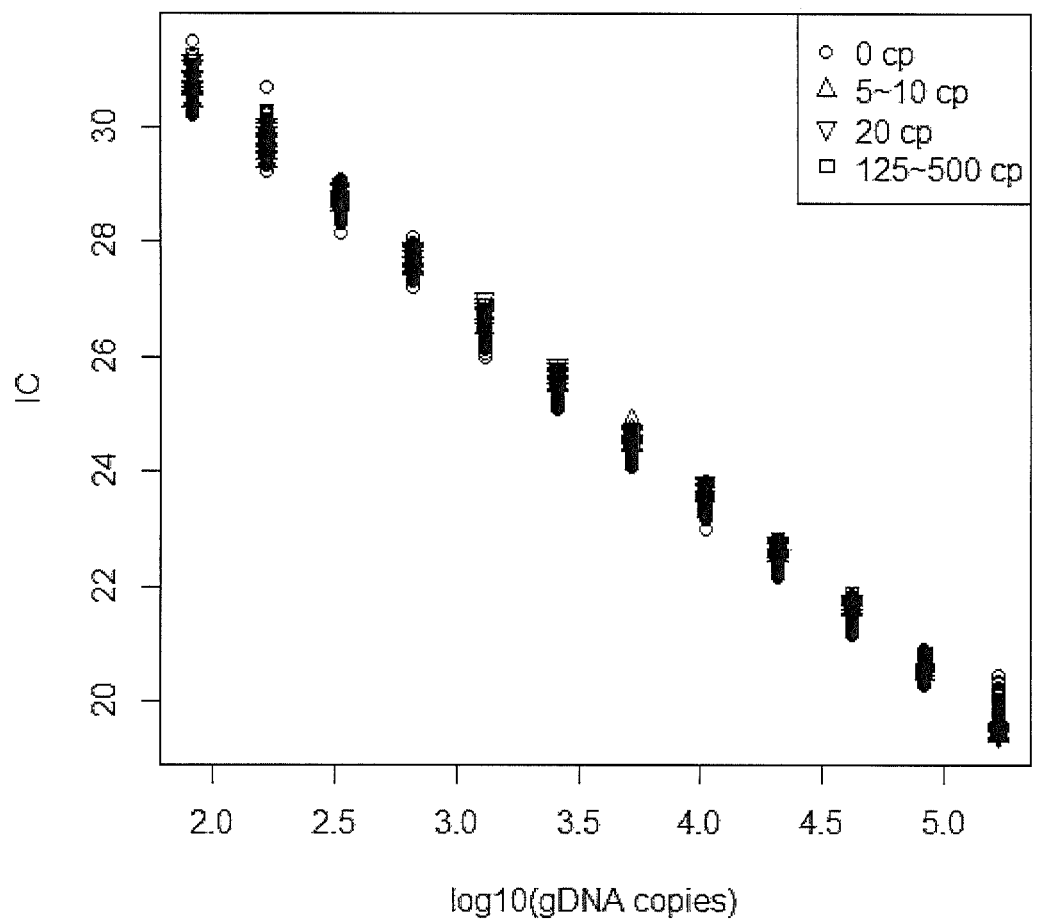
FIG. 2C. Relationship between the $C_t$ value for the control nucleic acid and initial DNA input for the EGFR mutation S786I target (training data set).
Figure 3A:
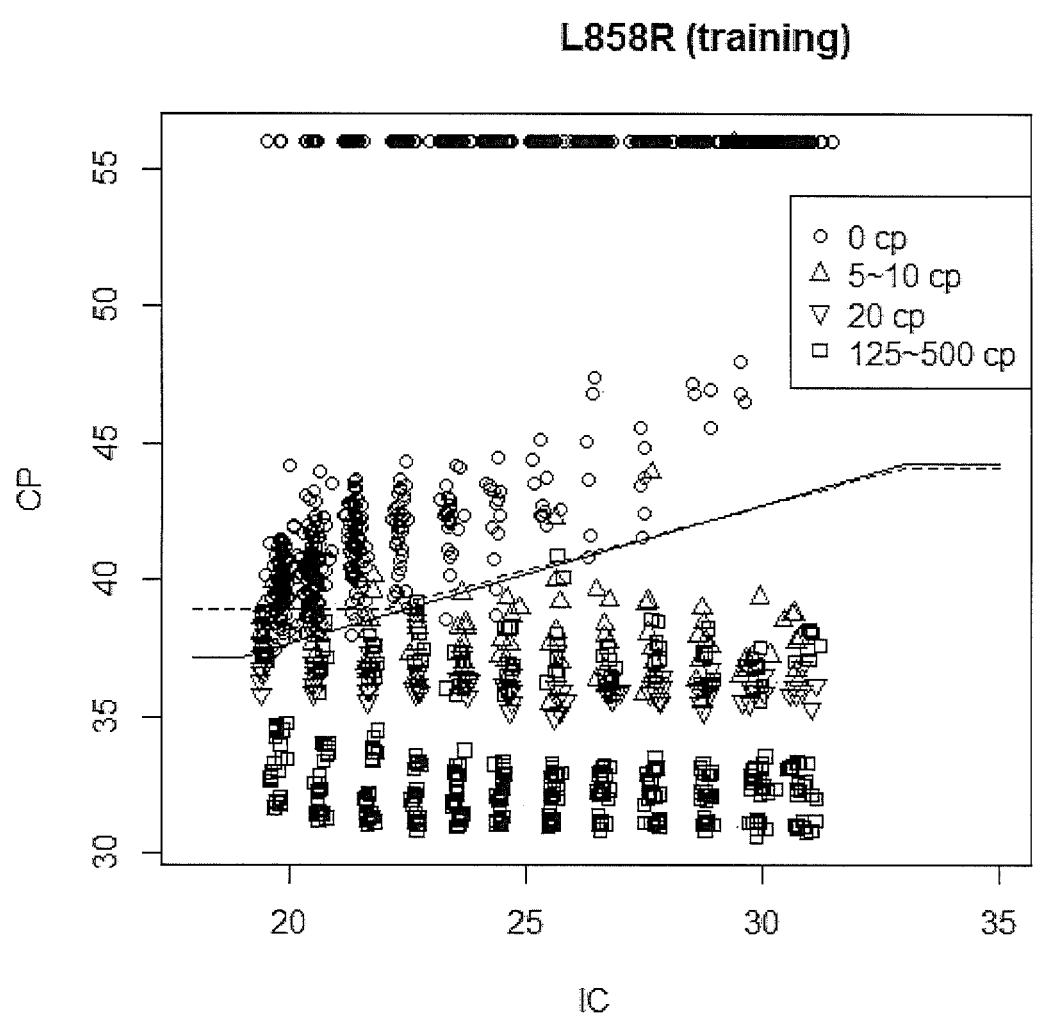
FIG. 3A. Relationship between the $C_t$ values for the target and control nucleic acids for the EGFR mutation L858R target (training data set).
Figure 3B:
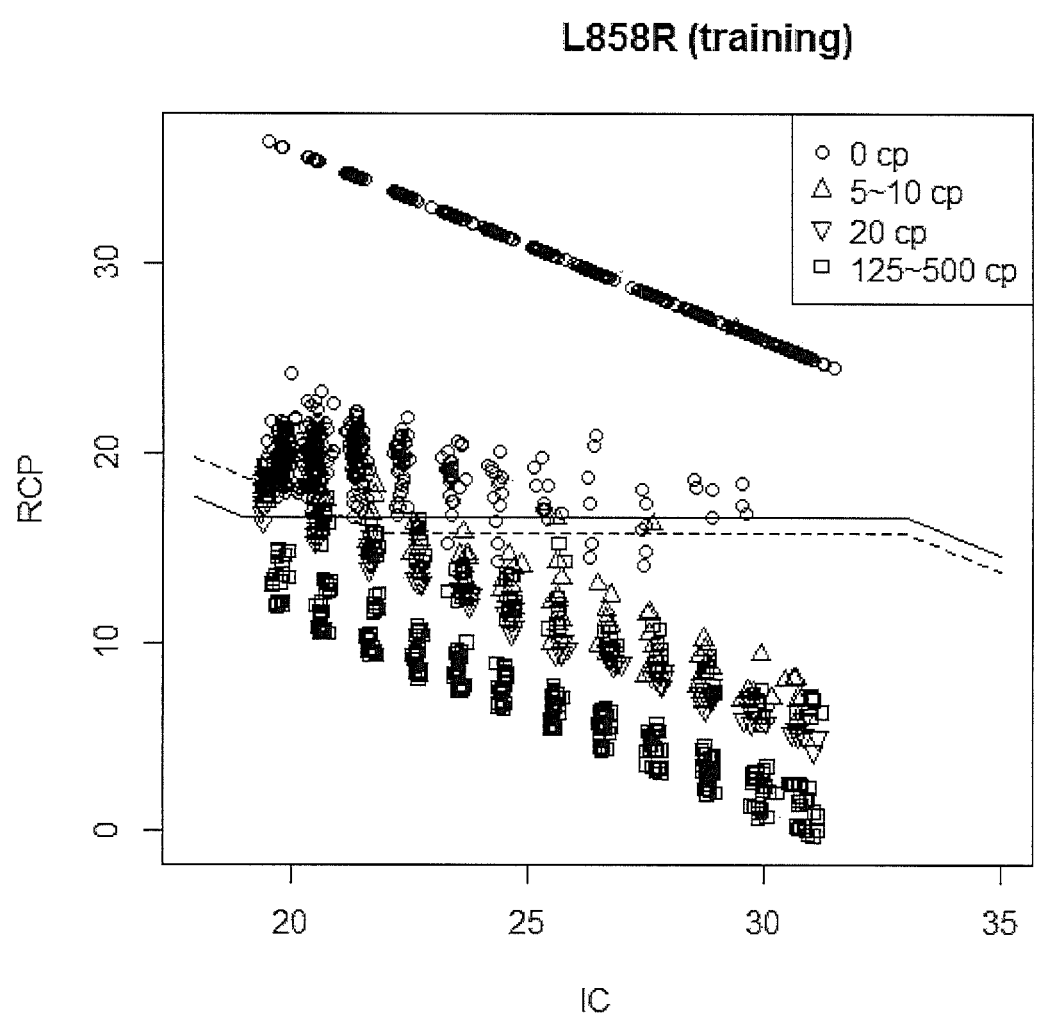
FIG. 3B. Relationship between the relative $C_t$ value for the target nucleic acid and the $C_t$ value for the control nucleic acid for the EGFR mutation L858R target (training data set).
Figure 3C:
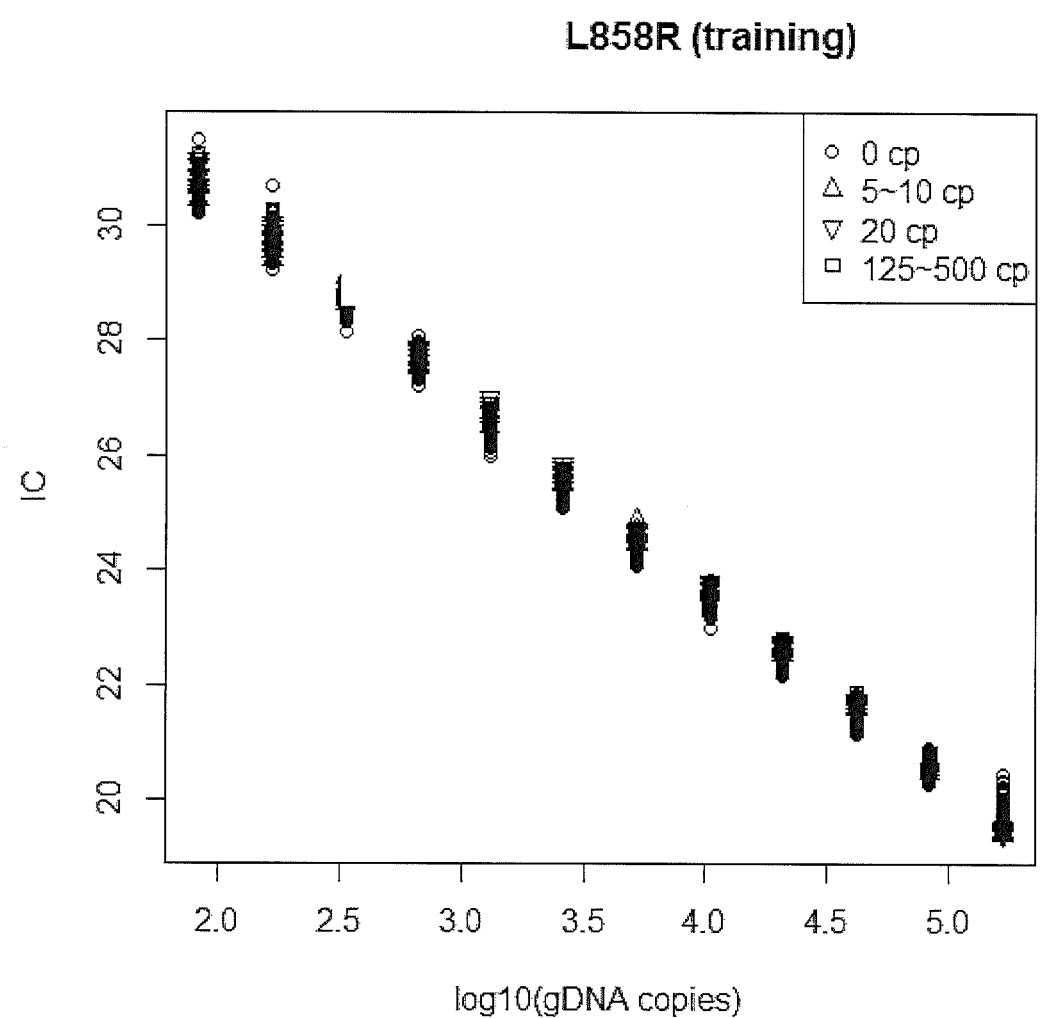
FIG. 3C. Relationship between the $C_t$ value for the control nucleic acid and initial DNA input for the EGFR mutation L858R target (training data set).

FIGS. 1(A-C), 2(A-C) and 3 (A-C) illustrate the method as applied to three training data sets. In the graphs, the line represents the separator function $F(x)$ determined according to Formula 1. Open circles correspond to samples where the target nucleic acid is absent. Squares and triangles represent samples containing various amounts of the target nucleic acid. FIGS. 1A, 2A and 3A illustrate the relationship between the absolute $C_t$ values for the target and control nucleic acids (CP and IC). FIGS. 1B, 2B and 3B illustrate the relationship between the relative $C_t$ value for the target nucleic acid and $C_t$ value for the control nucleic acids (RCP and IC). The open circles appear above the separator line, i.e. the line separates the samples where the target is absent from the samples where the target is present. FIGS. 1C, 2C and 3C illustrate the experimentally determined relationship between the $C_t$ value for the control nucleic acid and the initial input of total nucleic acid, confirming the expected relationship between the two values.

Figure 4A:
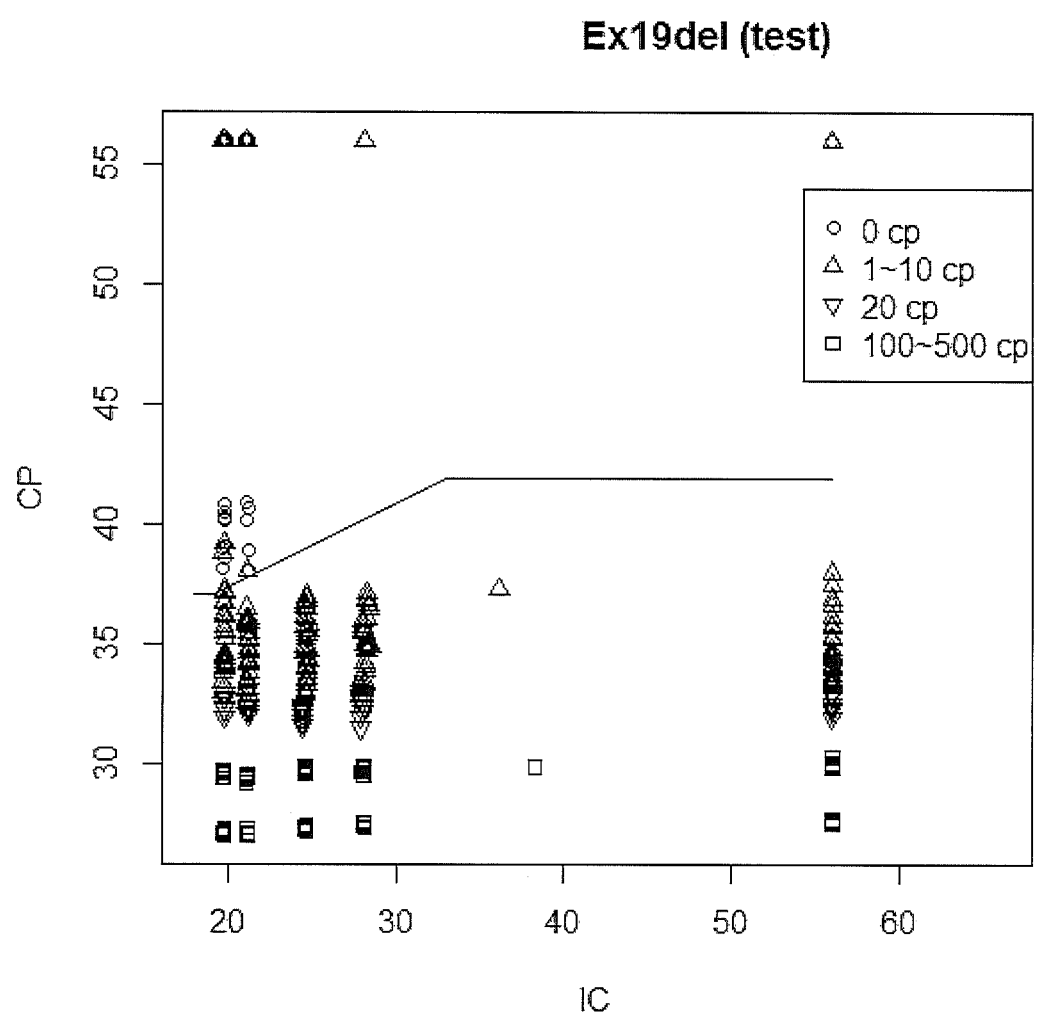
FIG. 4A. Relationship between the $C_t$ values for the target and control nucleic acids for the EGFR Exon 19 deletion target (testing data set)
Figure 4B:
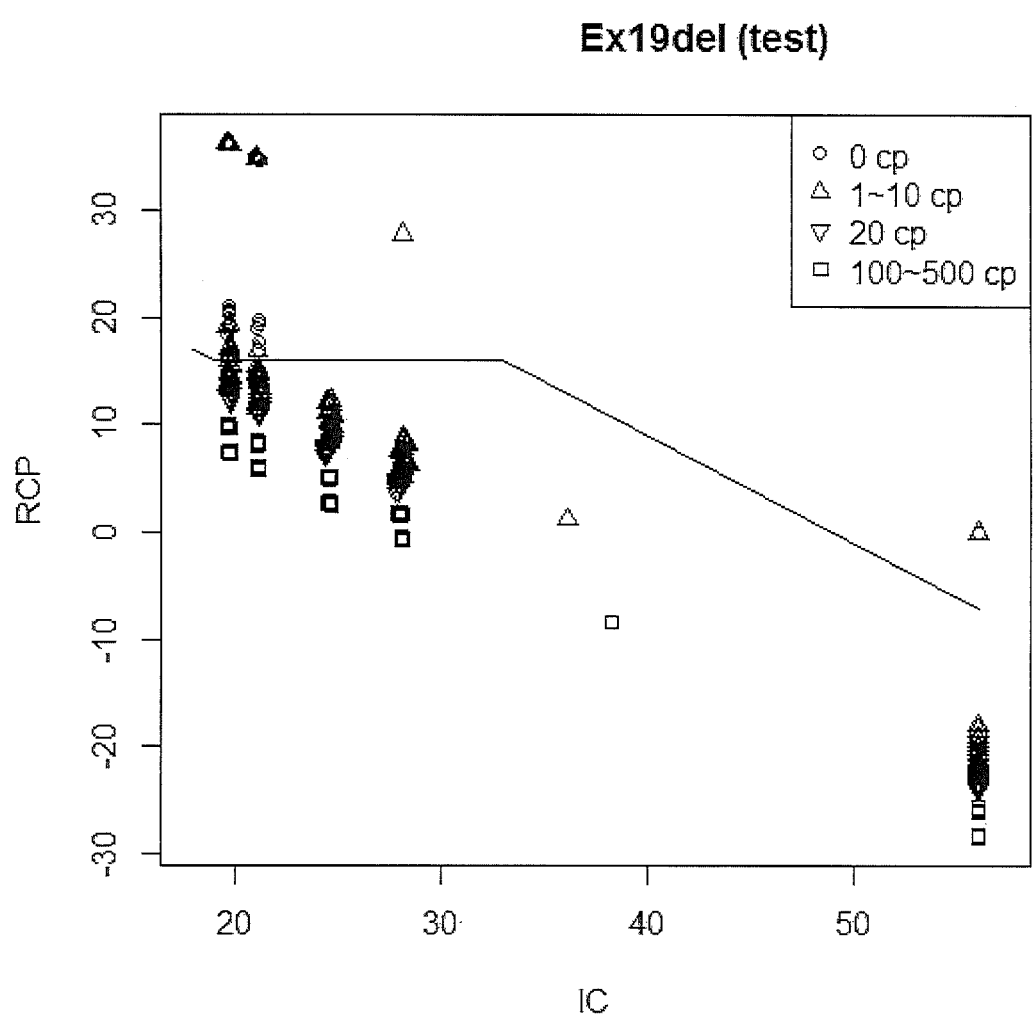
FIG. 4B. Relationship between the relative $C_t$ value for the target nucleic acid and the $C_t$ value for the control nucleic acid for the EGFR Exon 19 deletion target (testing data set).
Figure 5A:
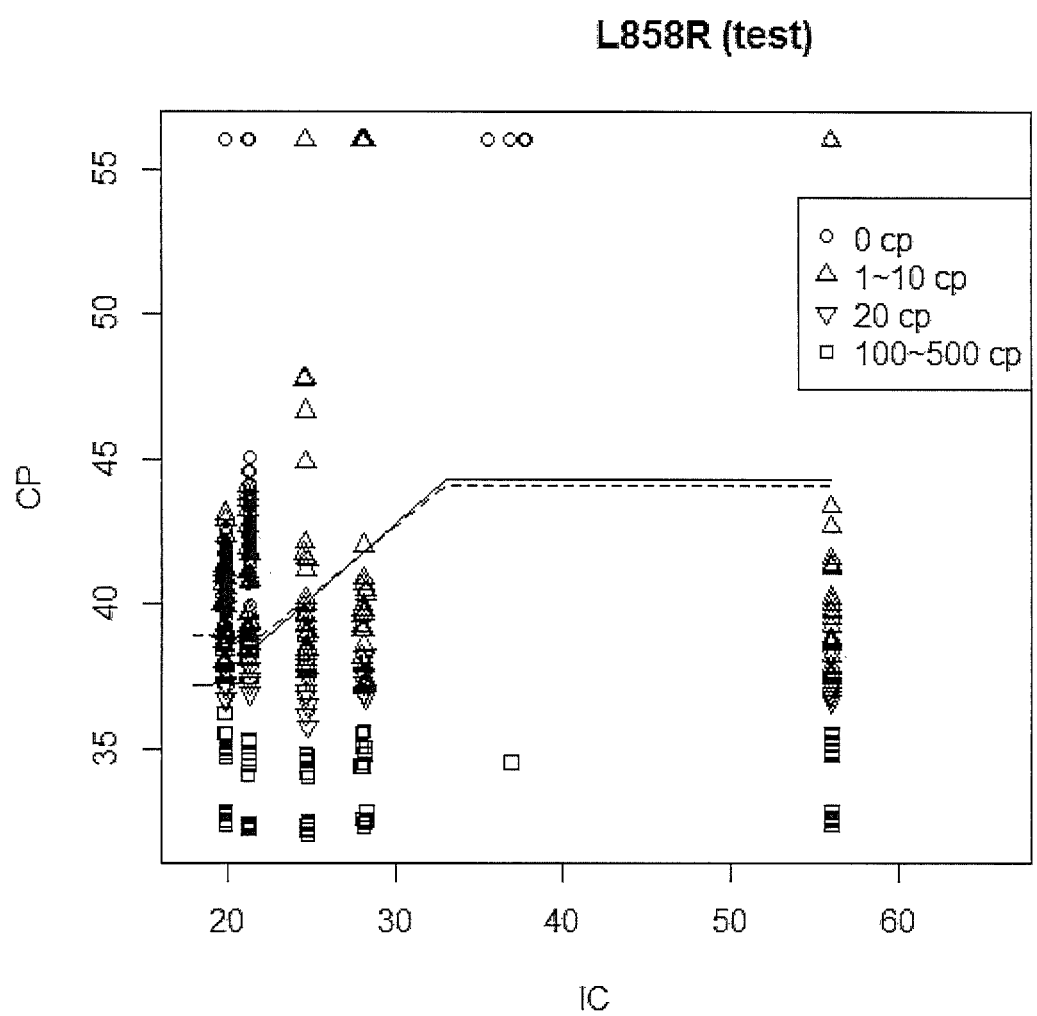
FIG. 5A. Relationship between the $C_t$ values for the target and control nucleic acids for the EGFR mutation L858R target (testing data set).
Figure 5B:
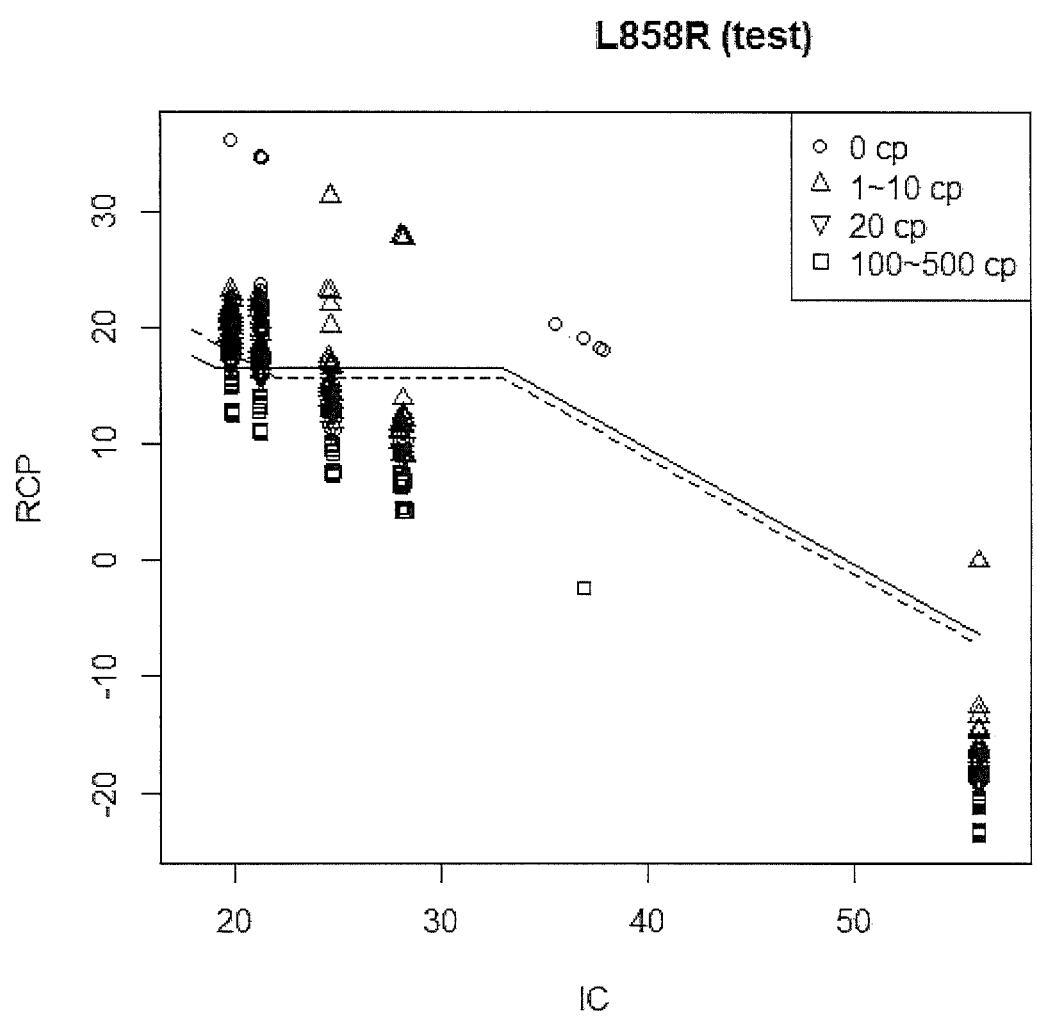
FIG. 5B. Relationship between the relative $C_t$ value for the target nucleic acid and the $C_t$ value for the control nucleic acid for the EGFR mutation L858R target (testing data set).
Figure 6A:
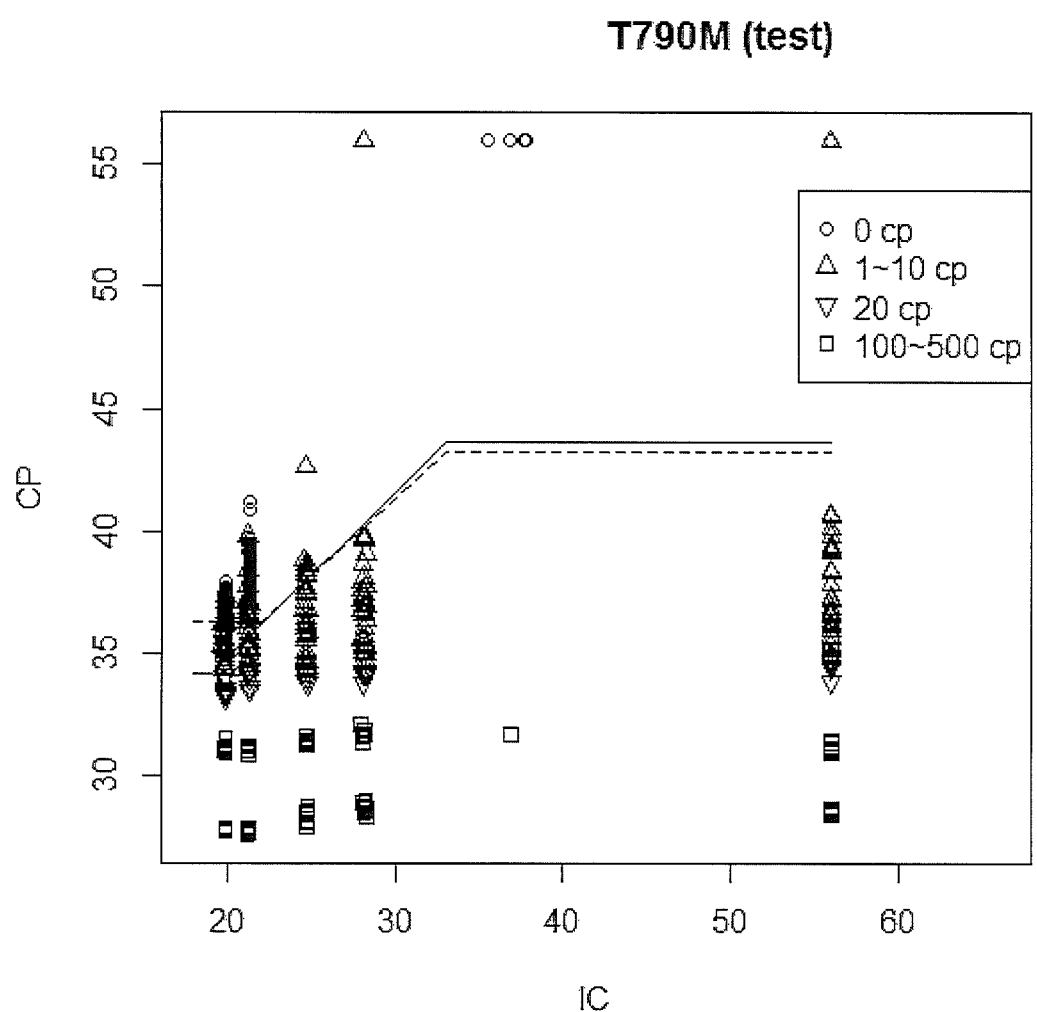
FIG. 6A. Relationship between the $C_t$ values for the target and control nucleic acids for the EGFR mutation T790M target (testing data set).
Figure 6B:
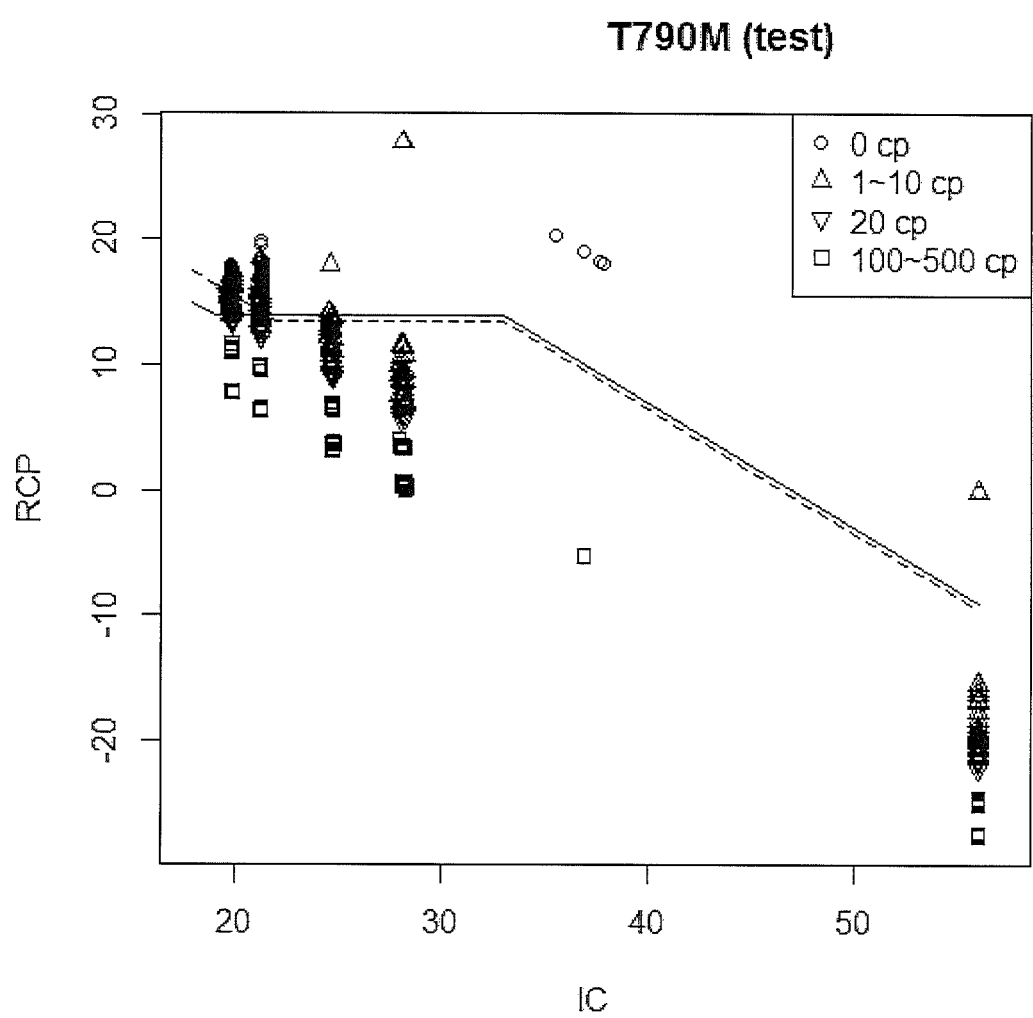
FIG. 6B. Relationship between the relative $C_t$ value for the target nucleic acid and the $C_t$ value for the control nucleic acid for the EGFR mutation T790M target (testing data set).

FIGS. 4(A-B), 5(A-B) and 6(A-B) illustrate application of the model developed using the training datasets to three testing data sets. As with training datasets, open circles correspond to samples where the target nucleic acid is absent. Squares and triangles represent samples containing various amounts of the target nucleic acid. FIGS. 4A, 5A and 6A illustrate the relationship between the absolute $C_t$ values for the target and control nucleic acids (CP and IC). FIGS. 4B, 5B and 6B illustrate the relationship between the relative $C_t$ value for the target nucleic acid and $C_t$ value for the control nucleic acids (RCP and IC). The function $F(x)$ aims to separate the samples where the target is absent from the samples where the target is present. It is apparent that the prediction made by the model is accurate: most open circles appear above the separator line.

In some embodiments, the amplification-dependent parameter used to determine the $C_t$ values is fluorescence of a probe specific for each of the target and control nucleic acids. In some embodiments, the probe is hydrolyzed by the a nucleic acid polymerase as described in Holland et al., (1991) *Proc. Natl. Acad. Sci.* 88:7276-7280 and U.S. Pat. No. 5,210, 015. Additionally, any other amplification-dependent measurable parameter may also be used to construct a growth curve and determine the $C_t$ value for each target nucleic acid.

In some embodiments, the invention comprises a data analysis algorithm for real-time PCR assays that detect mutations or single nucleotide polymorphisms (SNPs) contained in a target sequence by applying a learning statistical classifier system to a training set of data derived from a training set of samples, to build a general linear classifier to deliver a qualitative output reporting whether or not a mutation or SNP in the target nucleic acid is present in the sample. In further variations of this embodiment, the real-time PCR is allele-specific PCR (AS-PCR) (U.S. Pat. No. 6,627,402). In AS-PCR, several nucleic acids may be present in the sample, for example, a mutant and a wild-type sequence for a particular genetic locus. By virtue of having allele-specific primers, AS-PCR is capable of discriminating between the two sequences and preferentially (or exclusively) amplifying one of the sequences, while the other sequence is not amplified. AS-PCR assays typically include an internal control nucleic acid to guard against false-negative results. In such embodiments, the data imported into the learning statistical classifier system comprises $C_t$ values for the target nucleic acid and the control nucleic acid. In some embodiments, the accuracy of the general linear classifier can be improved by the use of constrains applied to the training set of samples, for example, constraints can be applied to the $C_t$ values for the control nucleic acid.

In some embodiments, the invention comprises a data analysis algorithm for real-time PCR assays that detect mutations in the kinase domain of the human EGFR gene (exons 18-21) by applying a learning statistical classifier system to a training set of samples to build a general linear classifier to deliver a qualitative output reporting whether or not the mutation are present in the sample. These mutations are associated with response to EGFR inhibitors used to treat certain human cancers. See e.g. Pao et al. (2004). "*EGF receptor gene mutations are common in lung cancers from "never smokers" and are associated with sensitivity of tumors to gefitinib and erlotinib*". P.N.A.S. 101 (36): 13306-13311; Sordella et al. (2004). "*Gefitinib-sensitizing EGFR mutations in lung cancer activate anti-apoptotic pathways*". Science 305 (5687): 1163-1167. In some embodiments, the sample is a blood sample. The invention comprises amplification of the target and control sequence in the sample by allele specific PCR with one or more pairs of primers that selectively hybridize to one or more of the mutations in the human EGFR gene that are described e.g. in Pao et al., and Sordella et al., supra, and in U.S. Pat. Nos. 7,294,468 and 7,960,118. In such embodiments, the data imported into the learning statistical classifier system comprises $C_t$ values for the target nucleic acid and the control nucleic acid. In some embodiments, the control nucleic acid is a sequence in the human EGFR gene that lies outside of the kinase domain and is not associated with frequent mutations. In some embodiments, the accuracy of the general linear classifier can be improved by the use of constrains applied to the $C_t$ values for the control nucleic acid training set of samples, for example, a single lower cut-off value of 19, 20, 21 or 22 is used. In other embodiments, a single upper cut-off value of 30, 31, 32 or 33 is used. In yet other embodiments, the range is 19-33, 20-33, 21-33, 22-33, 19-32, etc.

Examples and figures below illustrate applications of the method of the present invention to detecting mutations in the human EGFR gene. FIGS. 1(A-C), 2(A-C) and 3(A-C) represent training datasets, while FIGS. 4(A-B), 5(A-B) and 6(A-B) represent testing datasets where the target nucleic acid is a site of common mutation in the human EGFR gene. In FIGS. 1(A-C) and 4(A-B) the target is deletion in exon 19 of EGFR. In FIGS. 2(A-C) the target is EGFR mutation S768I. In FIGS. 3(A-C) and 5(A-B) the target is EGFR mutation L858R. In FIGS. 6(A-B) the target is EGFR mutation T790M.

In some embodiments, the invention is a computer readable medium including code for controlling one or more processors to classify whether a test sample contains a target nucleic acid according to the present invention. The code includes instructions to apply a learning statistical classifier system to a training data set in order to build a general linear classifier of Formula I, and then apply the general linear classifier of Formula I to the data from a test sample to produce a statistically derived decision classifying said sample as containing or not containing the target nucleic acid. The training data set comprises data from a training set of samples wherein the presence of various amounts or absence of the target nucleic acid and a control nucleic acid is known. The test samples are samples from one or more individuals wherein the presence and optionally, amount of the target nucleic acid is to be determined. In some embodiments, the data in each data set comprises measurements of an amplification-dependent parameter collected during PCR. In some embodiments, the learning statistical classifier system is support vector machine (SVM), linear discriminant analysis (LDA), or quadratic discriminant analysis (QDA).

In some embodiments, the invention is a system for detecting a target nucleic acid in a test sample according to the present invention comprising: a data acquisition module configured to produce a data set from a training set of samples and one or more test samples, the data set indicating presence and amount of the target nucleic acid and a control nucleic acid; a data processing unit configured to process the data by applying a learning statistical classifier system to the training data set in order to build a general linear classifier of Formula I, and then apply the general linear classifier of Formula I to the test data set comprising the data from the test sample, to produce a statistically derived decision classifying the test sample as containing or not containing the target nucleic acid; and a display module configured to display the data produced by the data processing unit.

In variations of this embodiment, the training data set used by the system comprises data from a training set of samples wherein the presence of various amounts or absence of the target nucleic acid and a control nucleic acid is known. The testing data set comprises data from one or more samples from one or more individuals wherein the presence and optionally, amount of the target nucleic acid is to be determined. In some embodiments, the data in each data set comprises measurements of an amplification-dependent parameter collected during PCR. In some embodiments, the learning statistical classifier system is SVM.

EXAMPLES

Example 1

Building a General Linear Classifier Model for Detecting the Presence of EGFR Mutations Using a Training Dataset Samples used for PCR comprised a mixture of wild-type genomic DNA extracted from human blood, and plasmids engineered to contain inserts of a portion of the human EGFR gene with various mutations listed in Table 1. A typical patient blood sample contains a large number of normal blood cells and rare circulating tumor cells as well as free circulating tumor DNA. To simulate a typical blood sample, each reaction mixture contained a varying number of copies of the wild-type DNA (400 to 100,000) representing normal cells, and a varying number of the plasmid copies (0, 2, 4, 5, 8, 10, 20, 50, 125) representing circulating tumor cells. PCR was conducted under standard conditions using COBAS® 4800 instrument (Roche Molecular Diagnostics, Inc., Indianapolis, Ind.). Internal control was a sequence in exon 28 of the human EGFR gene. Fluorescence data from the target and control template in each of the amplification reactions was automatically collected by the instrument and converted into $C_t$ data. The support vector machine (SVM) algorithm was used to generate the equation for the general linear classifier (Formula 1).

$$F(x)=w[0]+w[1]*x[1]+w[2]*x[2] \quad \text{Formula 1}$$

where F(x) is the decision function for sample x, x[1] is the $C_t$ value for the target nucleic acid, x[2] is the $C_t$ value for the control nucleic acid. Parameters w[0] and w[2] determined by the SVM are shown in Table 1. Parameter w[1] was set at 1. Optionally, a constraint comprising a cut-off value of 22 for the $C_t$ value for the internal control sequence was used. For comparison, a special linear classifier (Formula 2) was used.

$$G(x)=x[1]-x[2]-A \quad \text{Formula 2}$$

where G(x) is the decision function, x[1] is the $C_t$ value for the target nucleic acid, x[2] is the $C_t$ value for the control nucleic acid and A=w[0]/w[1].

It was determined that the best separation between the $C_t$ values of the samples containing the mutations and the samples not containing the mutations was achieved if the $C_t$ value of the control nucleic acid in the sample fell in the range between 19 and 33, more optimally between 22 and 30. In some samples, the constraint was set at 22, i.e. samples where the $C_t$ value for the control nucleic acid was less than 22 were not included in the calculation.

TABLE 1

Parameters for general and special classifiers determined using the training set.

| Mutation | Constraint | W[0] | W[1] | W[2] | A |
|---|---|---|---|---|---|
| Ex19del | None | −30.504 | 1 | −0.34625 | 15.995 |
| S768I | None | −31.363 | 1 | −0.25000 | 15.505 |
| L858R | None | −27.502 | 1 | −0.50853 | 16.625 |
| L858R | IC ≥ 22 | −28.550 | 1 | −0.47121 | 15.780 |
| T790M | None | −21.271 | 1 | −0.67857 | 14.030 |
| T790M | IC ≥ 22 | −22.561 | 1 | −0.62560 | 13.535 |

The model classifier built using the training set was subjected to three five-fold cross validations to determine accuracy. The average accuracy for each mutation is shown in Table 2. Accuracies for the general linear classifier (according to the invention) and the special linear classifier (according to the prior art) were compared. In Table 2, Accuracy A represents accuracy of the general linear classifier according to the invention and Accuracy B represents accuracy of the special linear classifier according to the prior art. The results show reproducible improvement in accuracy over the prior art.

TABLE 2

Results of the cross-validation of the model build in Example 1.

| Mutation | Constraint | N1 | N2 | N | Accuracy A | Accuracy B |
|---|---|---|---|---|---|---|
| Ex19del | None | 19 | 380 | 399 | 99.75 | 99.83 |
| S768I | None | 12 | 380 | 392 | 98.98 | 98.81 |
| L858R | None | 410 | 379 | 789 | 95.52 | 93.66 |
| L858R | IC ≥ 22 | 105 | 283 | 388 | 97.68 | 96.22 |
| T790M | None | 889 | 371 | 1260 | 93.17 | 91.51 |
| T790M | IC ≥ 22 | 529 | 275 | 804 | 95.56 | 93.78 |

N1 - non-mutant samples
N2 - mutant samples
N - total samples (N = N1 + N2)
IC - $C_t$ value for the control nucleic acid
Accuracy A - % accuracy of the model according to the invention (Formula 1)
Accuracy B - % accuracy of the model according to the prior art (Formula 2).

The results from the training datasets are further illustrated in FIGS. 1-3. FIGS. 1A-B, 2A-B and 3A-B show the decision function F(x) (separator, Formula 1) as a line on the plot CP vs. IC or the plot RCP vs. IC. Open circles represent samples that do not contain the target nucleic acids. As predicted by the model for the training sets, the line corresponding to F(x) separates samples that do not contain the target nucleic acid from samples that contain various amounts of the target nucleic acid (represented by squares and triangles). In FIGS. 1(A-C) the target is deletion in exon 19 of EGFR. In FIGS. 2(A-C) the target is EGFR mutation S768I. In FIGS. 3(A-C) the target is EGFR mutation L858R.

Example 2

Detecting the Presence of EGFR Mutations in a Testing Dataset Using the General Linear Classifier Model The special and general linear classifiers developed in Example 1 using the training set, were applied to an independent set of samples, also containing a mixture of normal genomic DNA and plasmids engineered to carry mutations. The samples were prepared and the PCR was conducted as in Example 1.

The testing set included a number of samples where $C_t$ value for the target nucleic acid was undetectable. (It exceeded the maximum $C_t$ value reportable by the instrument, which is 55 cycles.) For such samples the $C_t$ value was set at 56. The desired range for the $C_t$ value for the control nucleic acid were set at 19 or 22 at the lower end, and 33 at the higher end. If the $C_t$ value for the control nucleic acid fell outside of the desired range, the $C_t$ value was assigned a numerical value according to Formula 6. To include all the samples from the testing set, piece-wise linear classifiers (Formulas 4 and 5) were used.

$$F(x)=w[0]+w[1]*x[1]+w[2]*b(x[2]) \quad \text{Formula 4}$$

$$G(x)=x[1]-b(x[2])-A \quad \text{Formula 5}$$

where F(x) and G(x) are decision functions for sample x; x[1] is the $C_t$ value for the target nucleic acid, x[2] is the $C_t$ value for the control nucleic acid; parameters w[0], w[1] and w[2] were calculated using the training set (Table 1); A=w[0]/w[1]; and b(x[2]) is a piece-wise linear function determined according to Formula 6 where z is an independent variable for x[2]:

$$b(z) = \begin{cases} C_1, & \text{if } z < C_1, \\ z, & \text{if } C_1 \le z \le C_2, \\ C_2, & \text{if } z > C_2 \end{cases} \quad \text{Formula 6}$$

In the instant example, $C_1$ is 19 or 22 and $C_2$ is 33.

The average accuracy for each mutation in the testing set is shown in Table 3. Accuracies for the general linear classifier (according to the invention) and the special linear classifier (according to the prior art) were compared. In Table 3, Accuracy A represents accuracy of the general linear classifier and Accuracy B represents accuracy of the special linear classifier. The results show reproducible improvement in accuracy over the prior art.

TABLE 3

Results of applying the model from Example 1 to a testing set of samples.

| Mutation | Constraint applied to training set | N1 | N2 | N | Accuracy A | Accuracy B |
|---|---|---|---|---|---|---|
| Ex19del | None | 208 | 328 | 536 | 97.39 | 95.71 |
| L858R | None | 208 | 328 | 536 | 83.21 | 81.53 |
| L858R | IC ≥ 22 | 208 | 328 | 536 | 86.19 | 82.84 |
| T790M | None | 208 | 328 | 536 | 88.81 | 88.43 |
| T790M | IC ≥ 22 | 208 | 328 | 536 | 91.23 | 90.67 |

N1 - non-mutant samples
N2 - mutant samples
N - total samples (N = N1 + N2)
Accuracy A - % accuracy of the model according to the invention (Formula 4)
Accuracy B - % accuracy of the model according to the prior art (Formula 5)

The results are further illustrated in FIGS. 4(A-B), 5(A-B) and 6(A-B). These figures show the decision function F(x) (separator, Formula 1) as a line on the plot CP vs. IC or the plot RCP vs. IC. Open circles represent samples that do not contain the target nucleic acids. Validating the model, the line corresponding to F(x) effectively separates samples that do not contain the target nucleic acid from samples that contain various amounts of the target nucleic acid (represented by squares and triangles).

While the invention has been described in detail with reference to specific examples, it will be apparent to one skilled in the art that various modifications can be made within the scope of this invention. Thus the scope of the invention should not be limited by the examples described herein, but by the claims presented below.

What is claimed is:

1. A method of detecting a presence or absence of a target nucleic acid in a test sample comprising:
    (a) inputting, into a learning statistical classifier system, data from a training set of samples, where an amount of the target nucleic acid and a control nucleic acid is known, wherein the learning statistical classifier system includes one or more processors;
    (b) using the learning statistical classifier system, calculating a plurality of weights for a general linear classifier, wherein the general linear classifier for a sample x is defined as $F(x) = w[0] + w[1] \times x[1] + w[2] \times b(x[2])$;

wherein x[1] is a cycle-to-threshold (Ct) value for the target nucleic acid in sample x;
    wherein x[2] is a Ct value for the control nucleic acid in sample x;
    wherein the plurality of weights includes w[0], w[1] and w[2], w[1] and w[2] being independent of each other; and
    wherein b(x[2]) is a function of the Ct value x[2] for the control nucleic acid;
    (c) building the general linear classifier with the plurality of weights calculated by the learning statistical classifier system in step (b);
    (d) contacting the test sample with a reaction mixture containing reagents necessary to amplify the target and the control nucleic acids by polymerase chain reaction (PCR) under conditions enabling PCR;
    (e) measuring Ct values for the target and the control nucleic acids in the test sample to obtain a test set of data;
    (f) applying the general linear classifier built in step (c) to the test set of data obtained in step (e) to:
    determine a value for F(x) for the test sample based on the measured Ct value of the target nucleic acid and the measured Ct value of the control nucleic acid; and
    use the value for F(x) to classify the test sample as containing or not containing the target nucleic acid, thereby detecting the presence or absence of the target nucleic acid in the test sample.

2. The method of claim 1, wherein the learning statistical classifier system is selected from support vector machine (SVM), linear discriminant analysis (LDA) and quadratic discriminant analysis (QDA).

3. The method of claim 1, wherein the Ct values are measured by measuring fluorescence detected during each cycle of amplification.

4. The method of claim 1, wherein b(x[2]) is a piece-wise linear function defined as:

$$b(z) = \begin{cases} C_1, & \text{if } z < C_1 \\ z, & \text{if } C_1 \le z \le C_2, \\ C_2, & \text{if } z > C_2 \end{cases}$$

wherein $C_1$ is a lower threshold and $C_2$ is an upper threshold.

5. The method of claim 1, wherein b(x[2])=x[2].

6. The method of claim 1, wherein the target nucleic acid is a nucleic acid variant of a human sequence.

7. The method of claim 6, wherein the target nucleic acid is a mutant form of a human nucleic acid.

8. The method of claim 6, wherein the target nucleic acid comprises a mutation in the kinase domain of the human epidermal growth factor receptor (EGFR) gene.

9. The method of claim 1, further comprising:
    removing, from the data from the training set of samples before inputting the data from the training set of samples into the learning statistical classifier system, data for a sample in the training set of samples that has a Ct value for the control nucleic acid falling outside of a range.

10. The method of claim 1, wherein the control nucleic acid is a part of a same genome as the target nucleic acid.

11. A method of detecting a presence or absence of a target nucleic acid in a test sample comprising:
    (a) inputting, into a learning statistical classifier system, data from a training set of samples where an amount of the target nucleic acid and a control nucleic acid is known, wherein the learning statistical classifier system includes one or more processors;
    (b) using the learning statistical classifier system, calculating a plurality of weights for a general linear classifier, wherein the general linear classifier for a sample x is defined as $$F(x)=w[0]+w[1]\times x[1]+w[2]\times b(x[2]);$$

wherein x[1] is a Ct value for the target nucleic acid in sample x;

wherein x[2] is a Ct value for the control nucleic acid in sample x;

wherein the plurality of weights includes w[0], w[1] and w[2], w[1] and w[2] being independent of each other; and wherein b(x[2]) is a function of the Ct value x[2] for the control nucleic acid;

(c) building the general linear classifier with the plurality of weights calculated by the learning statistical classifier system in step (b);

(d) subjecting the test sample to polymerase chain reaction (PCR);

(e) measuring Ct values for the target and the control nucleic acids in the test sample to obtain a test set of data;

(f) applying the general linear classifier built in step (c) to the test set of data obtained in step (e) to determine a value for F(x) for the test sample based on the measured Ct value of the target nucleic acid and the measured Ct value of the control nucleic acid; and (g) classifying, using the value for F(x), the test sample as containing or not containing the target nucleic acid, thereby detecting the presence or absence of the target nucleic acid in the test sample.

12. A method of determining whether a target nucleic acid is present in a test sample comprising:

(a) subjecting a training set of samples wherein amounts of the target nucleic acid and a control nucleic acid are known to polymerase chain reaction (PCR) and measuring Ct values for the target and the control nucleic acids to obtain a training set of data;

(b) inputting, into a learning statistical classifier system, the training set of data obtained in step (a), wherein the learning statistical classifier system includes one or more processors;

(c) using the learning statistical classifier system, calculating a plurality of weights for a general linear classifier, wherein the general linear classifier for a sample x is defined as $$F(x)=w[0]+w[1]\times x[1]+w[2]\times b(x[2]);$$

wherein x[1] is a Ct value for the target nucleic acid in sample x;

wherein x[2] is a Ct value for the control nucleic acid in sample x;

wherein the plurality of weights includes w[0], w[1] and w[2], w[1] and w[2] being independent of each other; and wherein b(x[2]) is a function of the Ct value x[2] for the control nucleic acid;

(d) building the general linear classifier with the plurality of weights determined by the learning statistical classifier system in step (c);

(e) subjecting the test sample to PCR and measuring Ct values for the target and the control nucleic acids to obtain a test set of data;

(f) applying the general linear classifier built in step (d) to the test set of data obtained in step (e) to determine a value for F(x) for the test sample based on the measured Ct value of the target nucleic acid and the measured Ct value of the control nucleic acid; and (g) classifying, using the value for F(x), the test sample as containing or not containing the target nucleic acid.

13. A method of determining whether a target nucleic acid is present in a test sample comprising:

(a) subjecting a training set of samples wherein amounts of the target nucleic acid and a control nucleic acid are known to polymerase chain reaction (PCR) and measuring Ct values for the target and the control nucleic acids to obtain a training set of data;

(b) inputting into a learning statistical classifier system the training set of data obtained in step (a), wherein the learning statistical classifier system includes one or more processors;

(c) using the learning statistical classifier system, calculating a plurality of weights for a general linear classifier, wherein the general linear classifier for a sample x is defined as $$F(x)=w[0]+w[1]\times x[1]+w[2]\times b(x[2]);$$

wherein x[1] is a Ct value for the target nucleic acid in sample x;

wherein x[2] is a Ct value for the control nucleic acid in sample x;

wherein the plurality of weights includes w[0], w[1] and w[2], w[1] and w[2] being independent of each other; and wherein b(x[2]) is a function of the Ct value x[2] for the control nucleic acid;

(d) building the general linear classifier with the plurality of weights determined by the learning statistical classifier system in step (c);

(e) subjecting the test sample to PCR and measuring Ct values for the target and the control nucleic acids to obtain a test set of data;

(f) applying the general linear classifier built in step (c) to the test set of data obtained in step (e) to determine a value for F(x) for the test sample based on the measured Ct value of the target nucleic acid and the measured Ct value of the control nucleic acid; and (g) classifying, using the value for F(x), the test sample as containing or not containing the target nucleic acid.

14. A non-transitory computer readable medium including code for controlling one or more processors to classify whether a test sample contains a target nucleic acid, the code including instructions to:

(a) apply a learning statistical classifier system to a training data set including Ct values of the target nucleic acid and a control nucleic acid, in order to build a general linear classifier, wherein the learning statistical classifier system includes one or more processors;

wherein the general linear classifier for a sample x is defined as $$F(x)=w[0]+w[1]\times x[1]+w[2]\times b(x[2]);$$

wherein x[1] is a Ct value for the target nucleic acid in sample x;

wherein x[2] is a Ct value for the control nucleic acid in sample x;

wherein the plurality of weights includes w[0], w[1] and w[2], w[1] and w[2] being independent of each other; and wherein b(x[2]) is a function of the Ct value x[2] for the control nucleic acid; and (b) apply the general linear classifier built in step (a) to a testing data set comprising Ct values of the target nucleic acid and the control nucleic acid from the test sample to determine a value for F(x) for the test sample based on the Ct value of the target nucleic acid and the control nucleic acid from the test sample, and classify the test sample as containing or not containing the target nucleic acid using the value for F(x).

15. A system for detecting a target nucleic acid in a test sample comprising:
(a) a data acquisition module configured to produce a data set from a training set of samples and one or more test samples, the data set including Ct values of the target nucleic acid and a control nucleic acid in the training set of samples and the one or more test samples;
(b) a data processing unit configured to:
process the data set acquired by the data acquisition module by applying a learning statistical classifier system to a training data set of the data set acquired by the data acquisition module in order to build a general linear classifier F(x) defined as:

$F(x)=w[0]+w[1]\times x[1]+w[2]\times b(x[2])$, wherein x[1] is a Ct value for the target nucleic acid in sample x;
wherein x[2] is a Ct value for the control nucleic acid in sample x;
wherein the plurality of weights includes w[0], w[1] and w[2], w[1] and w[2] being independent of each other; and
wherein b(x[2]) is a function of the Ct value x[2] for the control nucleic acid; and
then apply the general linear classifier to a test data set comprising Ct values of the target nucleic acid and the control nucleic acid from the test sample, to determine a value for F(x) for the test sample based on the Ct value of the target nucleic acid and the control nucleic acid from the test sample, and classify, using the value for F(x), the test sample as containing or not containing the target nucleic acid;
(c) a display module configured to display the data produced by the data processing unit.

16. The system of claim 15, wherein b(x[2]) is a piece-wise linear function defined as:

$$b(z) = \begin{cases} C_1, & \text{if } z < C_1 \\ z, & \text{if } C_1 \leq z \leq C_2, \\ C_2, & \text{if } z > C_2 \end{cases}$$

wherein $C_1$ is a lower threshold and $C_2$ is an upper threshold.

17. The system of claim 15, wherein b(x[2])=x[2].

18. The system of claim 15, wherein the learning statistical classifier system is selected from support vector machine (SVM), linear discriminant analysis (LDA) and quadratic discriminant analysis (QDA).

19. The system of claim 15, wherein the Ct values are measured by measuring fluorescence detected during each cycle of amplification.

20. The system of claim 15, wherein the control nucleic acid is a part of a same genome as the target nucleic acid.

* * * * *